United States Patent
Virag et al.

(10) Patent No.: US 7,647,106 B2
(45) Date of Patent: Jan. 12, 2010

(54) DETECTION OF VASOVAGAL SYNCOPE

(75) Inventors: Nathalie Virag, Monnaz (CH); Rolf Vetter, Yverdon (CH); Richard Sutton, London (GB)

(73) Assignee: Medtronic, Inc., Minneapolis, MN (US)

( * ) Notice: Subject to any disclaimer, the term of this patent is extended or adjusted under 35 U.S.C. 154(b) by 555 days.

(21) Appl. No.: 10/422,069

(22) Filed: Apr. 23, 2003

(65) Prior Publication Data
US 2004/0215263 A1 Oct. 28, 2004

(51) Int. Cl.
*A61N 1/365* (2006.01)
(52) U.S. Cl. .................................................. 607/17
(58) Field of Classification Search .................... 607/17
See application file for complete search history.

(56) References Cited

U.S. PATENT DOCUMENTS

| | | | |
|---|---|---|---|
| 3,593,718 | A | 7/1971 | Krasner et al. |
| 4,009,721 | A | 3/1977 | Alcidi |
| 4,202,339 | A | 5/1980 | Wirtzfeld et al. |
| 4,228,803 | A | 10/1980 | Rickards |
| 4,312,355 | A | 1/1982 | Funke |
| 4,313,442 | A | 2/1982 | Knudson et al. |
| 4,428,378 | A | 1/1984 | Anderson et al. |
| 5,318,592 | A | 6/1994 | Schaldach |
| 5,419,338 | A | 5/1995 | Sarma et al. |
| 5,472,453 | A * | 12/1995 | Alt .................................. 607/4 |
| 5,501,701 | A | 3/1996 | Markowitz et al. |
| 5,626,624 | A | 5/1997 | Schaldach et al. |
| 5,797,840 | A * | 8/1998 | Akselrod et al. ............ 600/301 |
| 5,913,879 | A | 6/1999 | Ferek-Petric et al. |
| 5,919,210 | A * | 7/1999 | Lurie et al. ..................... 607/3 |
| 5,957,957 | A * | 9/1999 | Sheldon ......................... 607/17 |
| 5,991,659 | A | 11/1999 | de Vries et al. |

(Continued)

FOREIGN PATENT DOCUMENTS

EP 1062974 A2 6/2000

(Continued)

OTHER PUBLICATIONS

Vetter, R., et al. "Observer of Autonomic Cardiac Outflow Based on Blind Source Separation of ECG Parameters", *IEEE Transactions on Biomedical Engineering*, vol. 47, No. 5, pp. 578-582, May 2000.

(Continued)

*Primary Examiner*—Angela D Sykes
*Assistant Examiner*—Michael Kahelin
(74) *Attorney, Agent, or Firm*—Stephen W. Bauer

(57) ABSTRACT

It has been discovered that a change in posture that results in an increase in orthostatic stress, when followed by a withdrawal of sympathetic nervous activity, may indicate a future onset of vasovagal syncope (VVS). The invention is directed to devices and techniques for early detection of an episode of VVS so that therapies may be applied in advance of the episode to prevent the episode from occurring. Detection of a posture transition triggers a device such as an implanted pacemaker to determine an indicator of an autonomic nervous system activity of the patient. As a function of this determination, the device estimates a probability that the patient will experience VVS. When the probability exceeds a threshold, preventative therapy may be applied to address the VVS and to reduce the risk that the patient will faint.

30 Claims, 7 Drawing Sheets

U.S. PATENT DOCUMENTS

| | | | |
|---|---|---|---|
| 6,049,735 | A | 4/2000 | Hartley et al. |
| 6,078,834 | A | 6/2000 | Lurie et al. |
| 6,259,948 | B1 | 7/2001 | Florio et al. |
| 6,263,243 | B1 | 7/2001 | Lang |
| 6,405,085 | B1 | 6/2002 | Graupner et al. |
| 6,662,047 | B2 * | 12/2003 | Sorensen et al. .............. 607/18 |
| 6,719,701 | B2 | 4/2004 | Lade |
| 2003/0040774 | A1 | 2/2003 | Terry, Jr. et al. |
| 2003/0088164 | A1 * | 5/2003 | Stetson ....................... 600/323 |

FOREIGN PATENT DOCUMENTS

| | | |
|---|---|---|
| EP | 1 291 036 A2 | 3/2003 |

OTHER PUBLICATIONS

PCT Search Report, PCT/US2004/010804, 4 pgs.

H. Tanaka, et al., "Haemodynamic Changes During vasodepressor syncope in children and autonomoc function", *Clinical Phsiology*, vol. 17, No. 2, 1997, pp. 121-133.

Raefaello Furlan, M.D., et al., Cardiac Autonomic Patterns Preceding Occasional Vasovagal Reactions in Healthy Humans:, *Circulation*, vol. 98, 1998, pp. 1756-1761.

C. Kouakam et al., "Inadequate sympathovagal balance in response to orthostatism in patients with unexplained syncope and a positive head up tilt test", *Heart*, vol. 82, No. 3., Sep. 1999, pp. 312-318.

* cited by examiner

DETECTION OF VASOVAGAL SYNCOPE

FIELD OF THE INVENTION

The invention relates to medical methods and medical devices, and more particularly, to medical methods and medical devices to detect and treat vasovagal syncope (VVS).

BACKGROUND OF THE INVENTION

Vasovagal syncope (VVS) is a condition marked by a sudden drop in blood pressure resulting in fainting. It is not only unpleasant for the patient, but also potentially dangerous, as fainting may lead to injuries from falls. Some patients are at risk of recurrent episodes of VVS, and for them, VVS may present a serious impediment to daily activities and enjoyment of life.

Therapy to counteract VVS may include delivery of a drug to address the VVS. In patients having an implanted cardiac pacemaker, therapy may include pacing the heart to increase the heart rate and thereby increase the cardiac output to compensate for a drop in blood pressure. These techniques are generally more effective when applied well before the onset of an episode of VVS. If the therapies are not applied well before the onset of VVS, the therapies may not be effective in preventing the patient from fainting. The onset of the fainting spell may be marked by a sudden drop in heart rate or blood pressure, but by the time a drop in heart rate or blood pressure is detected, it is often too late to prevent the fainting spell.

BRIEF SUMMARY OF THE INVENTION

In general, the invention is directed to devices and techniques for reliably detecting the onset of VVS so that therapies will have time to address VVS before it occurs. It has been discovered that a change in the posture of the patient and a subsequent withdrawal of sympathetic activity may precede an episode of VVS. In particular, a change in posture that results in an increase in orthostatic stress, when followed by inadequate regulation of the neuro-cardiovascular system, may precede an onset of VVS.

The invention provides for detection of the onset of VVS by monitoring the posture of the patient and by observing an indicator of autonomic nervous system (ANS) activity of the patient, such as normalized cardiac sympathetic activity. The invention further may take into account physiological signal such as heart rate and blood pressure when detecting an onset of VVS. When an onset of VVS is detected, a medical device may deliver preventative therapy to address the VVS.

Ordinarily, observation of the ANS involves determination of an indicator of normalized ANS activity after a detected posture change. Following the detected posture change, a monitoring period may commence during which a baseline indicator for ANS activity may be determined. The indicator of ANS activity may then be observed with respect to the baseline. Similarly, the physiological signals may be normalized with respect to physiological signals monitored during the monitoring period. Use of a monitoring period to normalize the indicator of ANS activity and the physiological signals may increase the reliability of predictions of VVS onsets and reduce the number of false alarms, and may therefore reduce the occurrences in which the medical device delivers preventative therapy unnecessarily.

It has further been discovered that patients at risk of recurrent episodes of VVS do not ordinarily experience fainting for several minutes after the change in posture. Rather, a withdrawal of sympathetic activity, such as cardiac sympathetic activity, occurs several minutes following the change in posture. The monitoring period may therefore take place for some time following the change in posture, with little risk of VVS occurring during the monitoring period.

The actual episode of VVS may take place several minutes after the change in ANS activity predicts the episode. When the change in ANS activity indicates that an episode of VVS is likely, preventative therapy may be administered to address the VVS. Applying the techniques of the invention, a medical device may apply preventative therapy well before the onset of VVS, so that the therapy may be more effective in preventing the patient from fainting. The therapy may include, for example, preventative cardiac pacing or drug delivery.

In one embodiment, the invention is directed to a method comprising detecting a posture transition of a patient, determining an indicator of an ANS activity of the patient, and estimating a probability that the patient will experience vasovagal syncope as a function of the determination.

Although the invention is not limited to any particular technique for determining an indicator of an ANS activity, some techniques have been found to be robust and reliable. In one such technique, the method of the invention includes detecting at least two physiological signals that include a sympathetic activity indicator and a parasympathetic activity indicator, and applying blind source separation to the physiological signals to determine a sympathetic activity indicator and a parasympathetic activity indicator. The physiological signals may include, for example, a heart rate, a heart interval and a blood pressure.

The method may further include determining a baseline for the indicator of the ANS activity after the posture transition. The indicator of the ANS activity is compared to the baseline indicator. The method may further include delivering therapy, such as preventative cardiac pacing and drug delivery, when the probability that the patient will experience VVS exceeds a threshold.

The invention also includes computer-readable medium comprising instructions for causing a programmable processor to carry out the method.

In another embodiment, the invention comprises a device that includes a first sensor to detect a posture transition of a patient, a second sensor to sense a physiological signal that includes an indicator of ANS activity, and a processor to determine the indicator of ANS activity and to estimate a probability that the patient will experience vasovagal syncope as a function of the determination. The first sensor may be an activity sensor such as an accelerometer, and the second sensor may sense physiological signals such as a heart rate, a heart interval or a blood pressure. The device may further comprise a therapy module that delivers therapy, such as a drug delivery module or preventative pacing apparatus.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
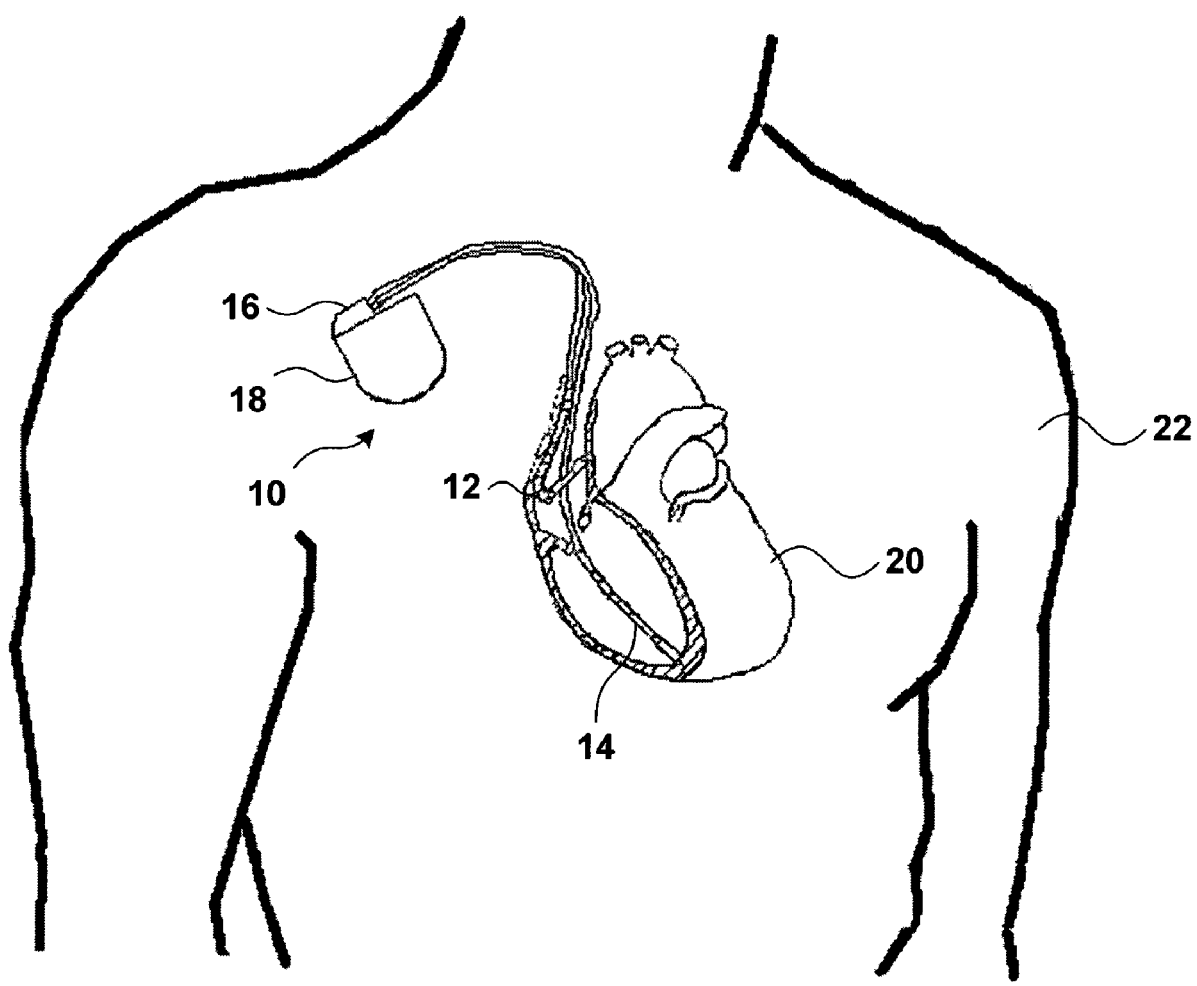
FIG. 1 is a schematic view of an exemplary implantable medical device that may practice the invention.

FIG. 1 is a schematic view of one embodiment of a device that may practice the invention. Implantable medical device ("IMD") 10 is a pacemaker comprising at least one of atrial pacing and sensing lead 12, ventricular pacing and sensing lead 14, or both, attached to connector module 16 of hermetically sealed enclosure 18 and implanted near human or mammalian heart 20 of a patient 22. Pacing and sensing leads 12 and 14 sense electrical signals attendant to the depolarization and repolarization of the heart 20, and further provide pacing pulses for causing depolarization of cardiac tissue in the vicinity of the distal ends thereof. Leads 12 and 14 may have unipolar or bipolar electrodes disposed thereon.

IMD 10 is one example of a device that may be employed to supply therapy to treat vasovagal syncope (VVS). In particular, IMD 10 may deliver pacing pulses to heart 20 to cause heart 20 to beat at a rate faster than the intrinsic rate of heart 20. By maintaining a high heart rate, IMD 10 may maintain high cardiac output when patient 22 experiences VVS, and thereby reduce the risk that patient 22 will faint, i.e., lose consciousness.

The invention is not limited to application with a dual-chamber pacemaker such as IMD 10, however. The invention may be applied to a variety of external or implantable devices, including multi-chamber pacemakers. Devices other than pacemakers, such as external or implantable drug delivery devices, may also apply the techniques of the invention to detect the onset of VVS and apply therapy to reduce the risk that patient 22 will faint.

Figure 2:
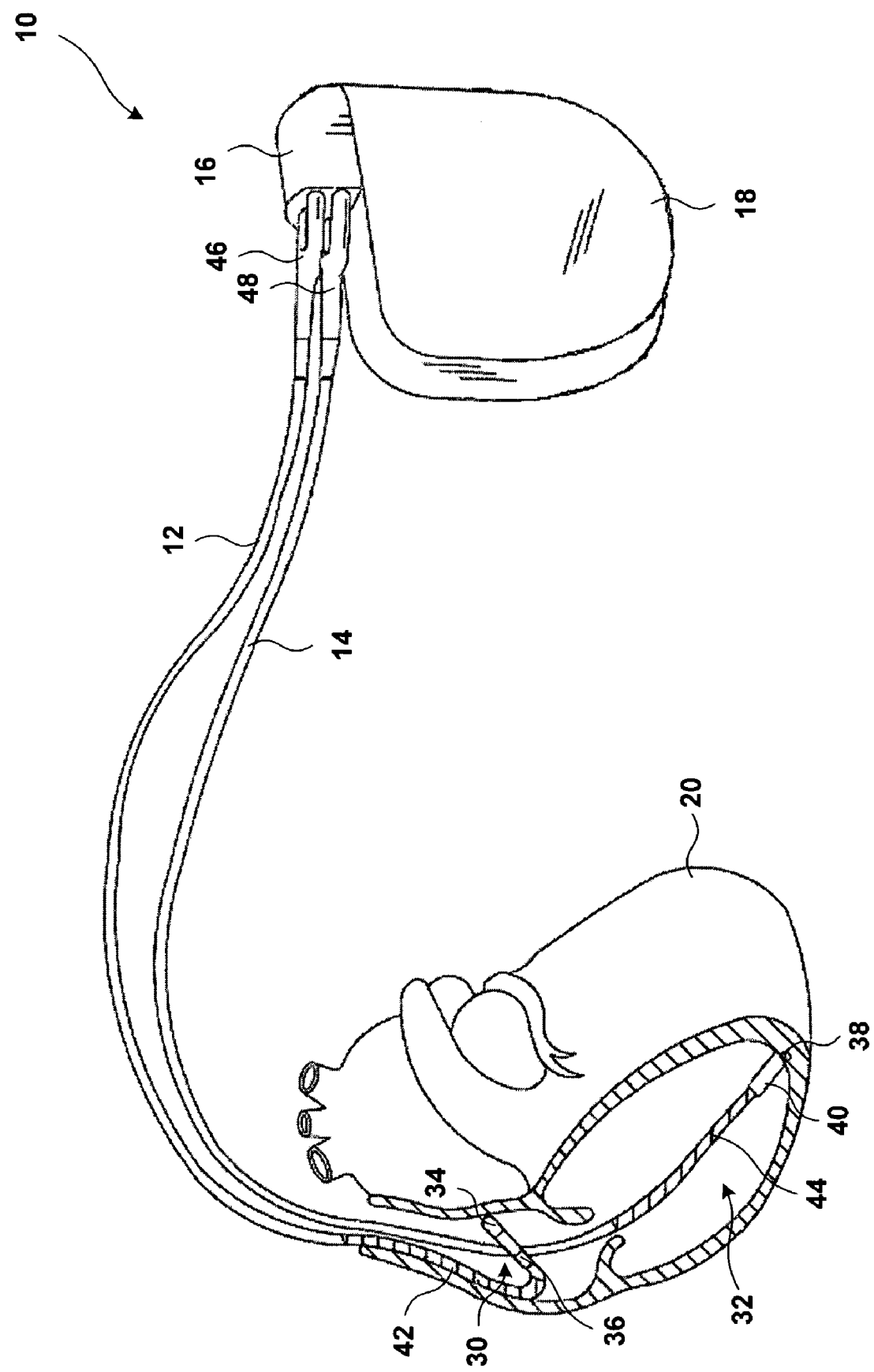
FIG. 2 shows the implantable medical device located in and near a heart.

FIG. 2 shows IMD 10, with connector module 16 and hermetically sealed enclosure 18 located in and near human or mammalian heart 20. Atrial and ventricular pacing leads 12 and 14 extend from connector module 16 to the right atrium 30 and right ventricle 32, respectively, of heart 20. Atrial electrodes 34 and 36 disposed at the distal end of atrial pacing lead 12 are located in right atrium 30. Ventricular electrodes 38 and 40 disposed at the distal end of ventricular pacing lead 14 are located in right ventricle 32. Pulse generators (not shown in FIG. 2) inside enclosure 18 generate pacing pulses. The pacing pulses are delivered to right atrium 30 or right ventricle 32 by electrodes 34, 36, 38, 40.

When addressing a possible episode of VVS, the pacing pulses may maintain a high cardiac output and reduce the risk that patient 22 will faint. Pacing heart 20 to prevent the undesirable effects of VVS is called "preventative pacing." The pacing generators and associated leads and electrodes are an example of a therapy module that can deliver therapy to patient 22 to address VVS.

In addition to pacing, IMD 10 may apply other forms of therapy, which need not be related to treatment of VVS. In FIG. 2, for example, atrial lead 12 and ventricular lead 14 include defibrillation electrodes 42 and 44, respectively. Defibrillation electrodes 42 and 44 deliver defibrillation shocks to right atrium 30 or right ventricle 32.

Atrial and ventricular leads 12, 14 each include an elongated insulative lead body carrying one or more conductors insulatively separated from one another. At the proximal end of leads 12, 14 are bifurcated connectors 46, 48, which electrically couple the connectors to connector module 16 of IMD 10.

Figure 3:
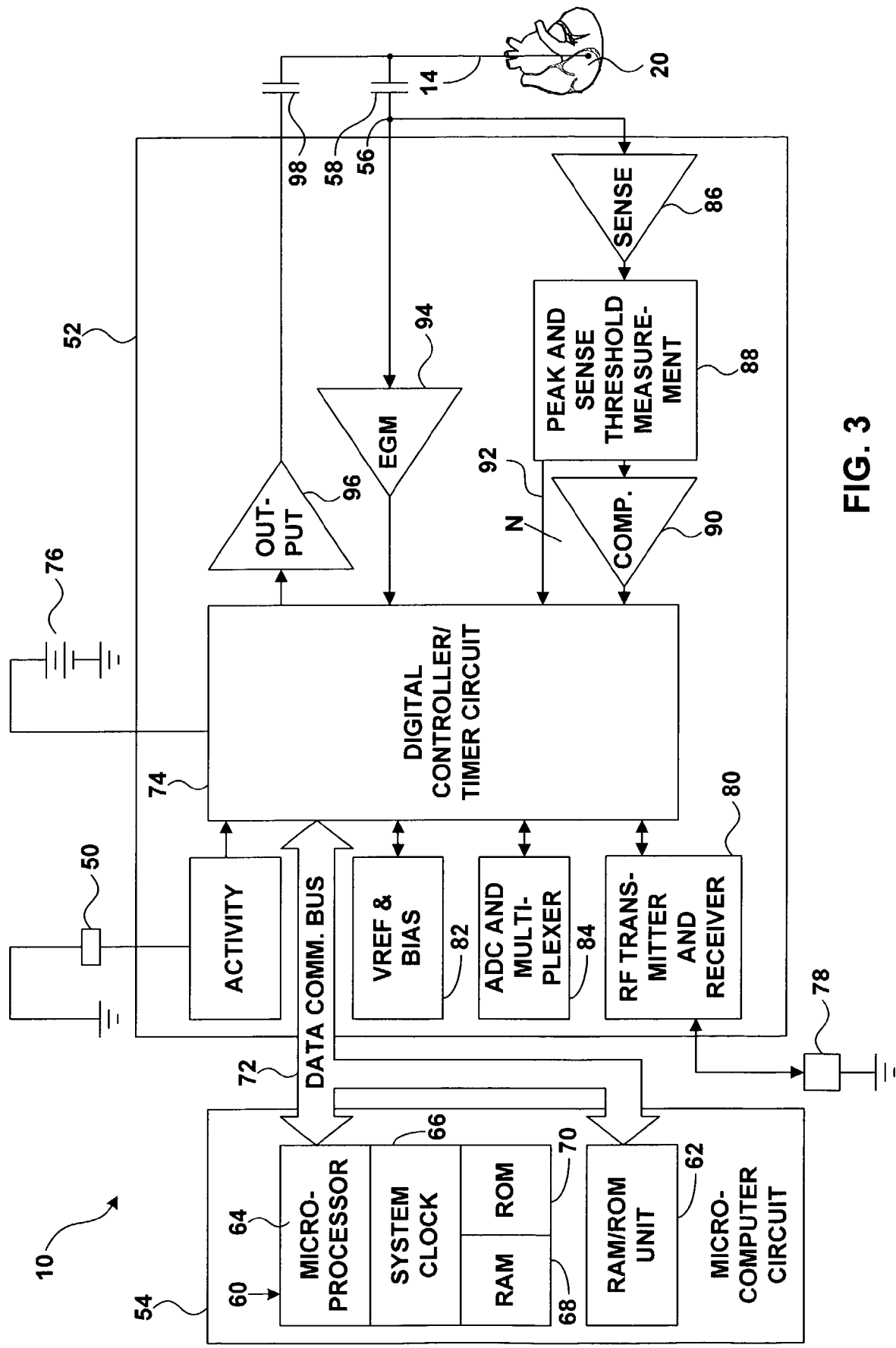
FIG. 3 is a block diagram illustrating the constituent components of the implantable medical device depicted in FIGS. 1 and 2.

FIG. 3 shows a block diagram illustrating the constituent components of IMD 10 in accordance with one embodiment of the invention, in which IMD 10 is a pacemaker having a microprocessor-based architecture. IMD 10 includes one or more activity sensors 50. Activity sensor 50 may include an accelerometer, such as an electrostatic accelerometer, a piezoceramic accelerometer or a microelectromechanical accelerometer, that typically provides a sensor output that varies as a function of a measured parameter relating to a patient's metabolic requirements. In other words, activity sensor 50 detects motion of patient 22 that accompanies physical activity, and may adjust the pacing rate to the metabolic needs associated with the physical activity.

In addition, activity sensor 50 is configured to detect a change in the posture of patient 22. Activity sensor 50 is configured to sense a posture transition that accompanies an increase in orthostatic stress. In general, orthostatic stress increases when patient 22 moves into a more upright position. As will be described below, an onset of orthostatic stress, followed by a determination that the ANS is inadequately regulating the cardiovascular system, are early predictors of a likely episode of VVS.

The output of activity sensor 50 is coupled to input/output circuit 52. Input/output circuit 52 contains analog circuits for interfacing with heart 20, activity sensor 50, and other components and circuits for the application of stimulating pulses to heart 20. The rate of heart 20 is controlled by software-implemented algorithms stored within microcomputer circuit 54.

For the sake of convenience, IMD 10 in FIG. 3 is shown with only lead 14 connected. Similar circuitry and connections not explicitly shown in FIG. 3 apply to lead 12 (shown in FIGS. 1 and 2), however. Lead 14 is coupled to node 56 in IMD 10 through input capacitor 58.

Microcomputer circuit 54 comprises on-board circuit 60 and off-board circuit 62. On-board circuit 60 preferably includes microprocessor 64, system clock circuit 66 and on-board random access memory (RAM) 68 and read-only memory (ROM) 70. Off-board circuit 62 comprises a RAM/ROM unit. On-board circuit 60 and off-board circuit 62 are each coupled by data communication bus 72 to digital controller/timer circuit 74. Microcomputer circuit 54 may comprise a custom integrated circuit device augmented by standard RAM/ROM components.

Electrical components shown in FIG. 3 are powered by an appropriate implantable battery power source 76. For the sake of clarity, the coupling of battery power to the various components of IMD 10 is not shown in FIG. 3.

Antenna 78 is connected to input/output circuit 52 to permit uplink/downlink telemetry through radio frequency (RF) transmitter and receiver telemetry unit 80. IMD 10 in FIG. 3 is programmable by an external programming unit (not shown in the figures) that communicates with IMD 10 via antenna 78 and RF transmitter and receiver telemetry unit 80.

VREF and Bias circuit 82 generates stable voltage reference and bias currents for analog circuits included in input/output circuit 52. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 52.

Digital controller/timer circuit 74 is coupled to sensing circuitry, including sense amplifier 86, peak sense and threshold measurement unit 88 and comparator/threshold detector 90. Sense amplifier 86 amplifies electrical cardiac signals sensed via lead 14 and provides an amplified signal to peak sense and threshold measurement circuitry 88, which in turn provides an indication of peak sensed voltages and measured sense amplifier threshold voltages on multiple conductor signal path 92 to digital controller/timer circuit 74. An amplified sense amplifier signal is also provided to comparator/threshold detector 90.

Digital controller/timer circuit 74 is further coupled to electrogram (EGM) amplifier 94 for receiving amplified and processed signals sensed by lead 14. The electrogram signal provided by EGM amplifier 94 is employed, for example, when IMD 10 is being interrogated by an external programmer to transmit a representation of a cardiac analog electrogram. Output pulse generator 96 provides amplified pacing stimuli to heart 20 through coupling capacitor 98 in response to a pacing trigger signal provided by digital controller/timer circuit 74.

IMD 10 may sense the R-R interval, i.e., the interval between ventricular activations, via sense amplifier 86, peak sense and threshold measurement unit 88 and comparator/threshold detector 90. The R-R interval is directly related to the rate at which heart 20 beats. Consequently, sense amplifier 86, peak sense and threshold measurement unit 88 and comparator/threshold detector 90 may serve as a heart rate sensor or a heart interval sensor. As will be described below, the R-R interval is a physiological signal that includes an indicator of autonomic nervous system (ANS) activity.

IMD 10 may sense other intervals as well, such as the Q-T interval. In some embodiments of the invention, the Q-T interval may be sensed via analysis of the electrogram signal from EGM amplifier 94. The Q-T interval likewise is a physiological signal that includes an indicator of ANS activity.

IMD 10 may further include one or more other sensors (not shown) to sense other physiological signals that include an indicator of ANS activity. Alternatively, IMD 10 may receive signals from one or more other sensors that sense other physiological signals. An example of such a sensor is a pressure sensor that responds to a blood pressure such as arterial blood pressure. Blood pressure is another physiological signal that includes an indicator of ANS activity. The pressure sensor may be disposed in a chamber of heart 20, e.g., on the distal end of lead 14, or may be deployed at another site in or around the cardiovascular system.

Figure 4:
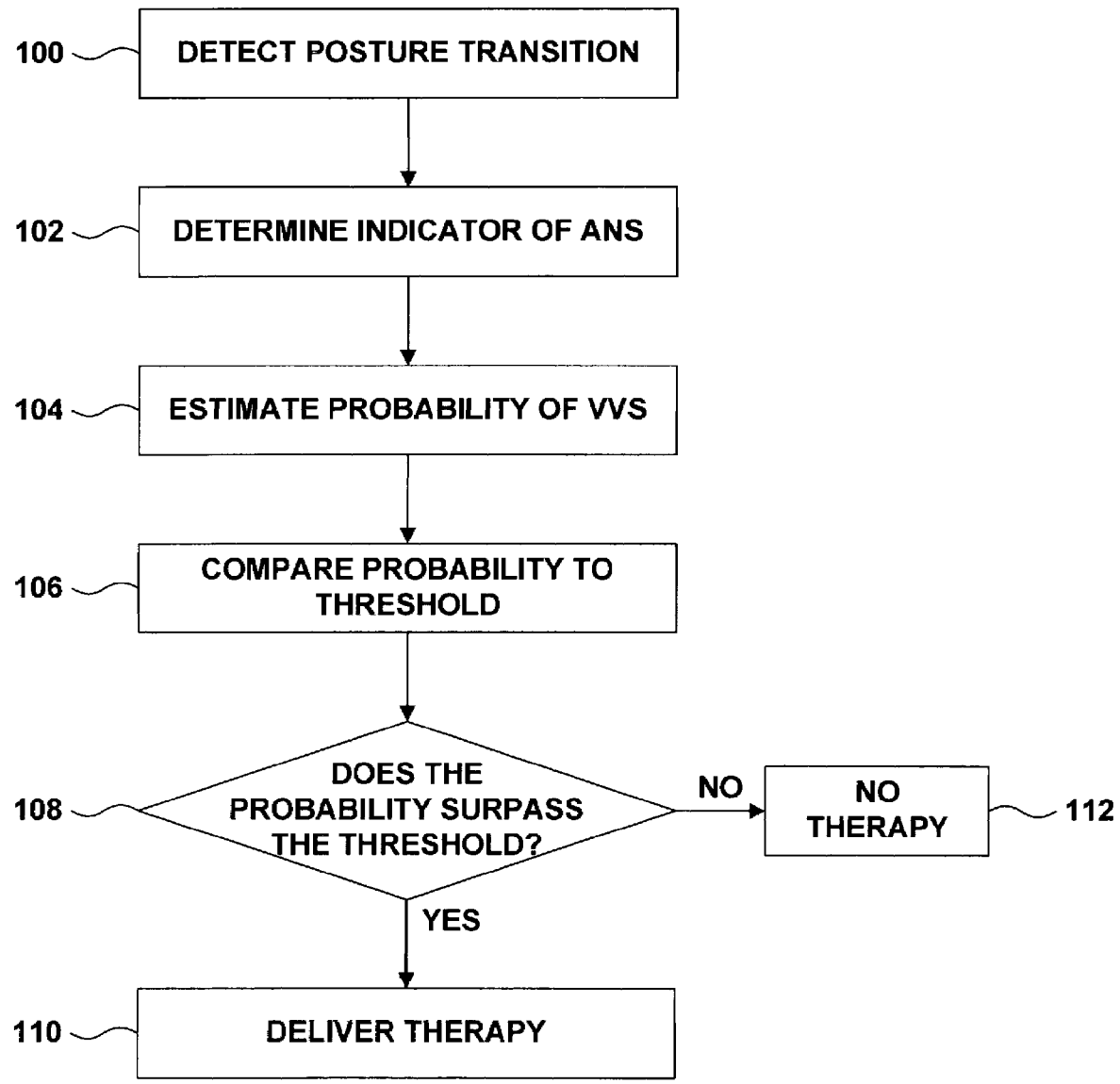
FIG. 4 is a flow diagram illustrating a technique for early detection and treatment of VVS according to an embodiment of the invention.

FIG. 4 is a flow diagram that illustrates techniques for reliably detecting the onset of VVS so that therapies will have time to address VVS and so that the risk of fainting may be reduced. The ANS activity of the patient, when preceded by a change in posture, may signal the likely onset of VVS. In general, the ANS consists of two subdivisions, the sympathetic nervous system and the parasympathetic nervous system. Both the sympathetic and parasympathetic nervous systems are active in a typical patient to some degree. Under some conditions, however, sympathetic nervous system activity is dominant over parasympathetic nervous system activity, and under other conditions, parasympathetic nervous system activity is dominant over sympathetic nervous system activity. The dominance of the sympathetic system over the parasympathetic nervous system, or vice versa, is called the "balance between sympathetic and parasympathetic activity," or "sympatho-vagal balance" for short. "Vagal" refers to the vagus nerve, which serves as the major nerve of the parasympathetic nervous system.

In general, the sympathetic system promotes responses that prepare the body for strenuous physical activity, such as physical activity that may be required in a stressful or emergency situation. The parasympathetic system is generally dominant in relaxed situations.

Sympathetic or parasympathetic dominance may vary from organ to organ, i.e., a discrete organ such as the heart may experience a shift in the balance between sympathetic and parasympathetic activity, even if other organs do not. Sympathetic stimulation on the heart generally results in an increased heart rate and increased force of contraction, while parasympathetic stimulation of the heart generally has the opposite effect. Sympathetic stimulation also results in constriction of blood vessels for most organs, and dilation of blood vessels serving the heart.

It has been discovered that a withdrawal of cardiac sympathetic activity and an increase in cardiac parasympathetic activity may precede an episode of VVS. With parasympathetic activity rising, heart rate may drop and blood vessels may be less constricted, resulting in a drop in blood pressure. A drop in heart rate and blood pressure typically precedes an episode of VVS.

Declines in heart rate and blood pressure, taken by themselves, are unreliable predictors of a risk of VVS. A patient may experience a drop in heart rate and blood pressure, but still receive enough sympathetic stimulation to avoid fainting. Similarly, a change in the sympatho-vagal balance is not always a reliable predictor of a risk of VVS. It has been discovered that a change in the posture of the patient, followed by a change in the sympatho-vagal balance, is a good predictor of a risk of VVS, when combined with an analysis of neuro-cardiovascular modulation. In particular, it has been discovered that it is possible to predict a risk of VVS by detecting a change in posture, followed by determining that the ANS is inadequately regulating the cardiovascular system.

Accordingly, a change in the posture of the patient (100) triggers a determination of an indicator of ANS activity (102). In particular, when a sensor such as activity sensor 50 in IMD 10 detects a change in posture, a processor such as microcomputer circuit 54 in IMD 10 analyzes the ANS activity, and estimates a probability that an episode of VVS will occur (104). Details of exemplary analysis and estimation techniques will be described below. Generally speaking, the analysis and estimation result in more reliable predictors of VVS when the analysis of ANS activity is based upon a cumulative measure of a particular ANS indicator and physiological signals.

The probability that an episode of VVS will occur may be compared to a threshold (106). If the probability that an episode of VVS will occur surpasses the predetermined threshold (108), then a device such as IMD 10 may deliver therapy (110), such as preventative pacing. If the probability that an episode of VVS will occur does not surpass the predetermined threshold (108), then no therapy is delivered (112).

Determination of an indicator of ANS activity (102) may be accomplished in many ways. The techniques described below are not the only possible techniques for determining an indicator of ANS activity.

One indicator of ANS activity may be the sympatho-vagal balance. Accordingly, a processor such as microcomputer circuit 54 may determine ANS activity by determining the sympatho-vagal balance. ANS activity may also be reflected by individual indicators of sympathetic and parasympathetic activity. Accordingly, a processor such as microcomputer circuit 54 may determine a sympathetic activity indicator and a parasympathetic activity indicator, and may estimate the relative magnitude of the sympathetic activity indicator in comparison to the parasympathetic activity indicator. The indicators may reflect sympathetic or parasympathetic activity in a particular organ, e.g., the indicators may reflect cardiac sympathetic nervous activity and cardiac parasympathetic nervous activity. It may also be possible to determine an indicator of ANS activity by looking solely at sympathetic or parasympathetic activity. The invention is not limited to any particular technique for determining an indicator of ANS activity.

Figure 5:
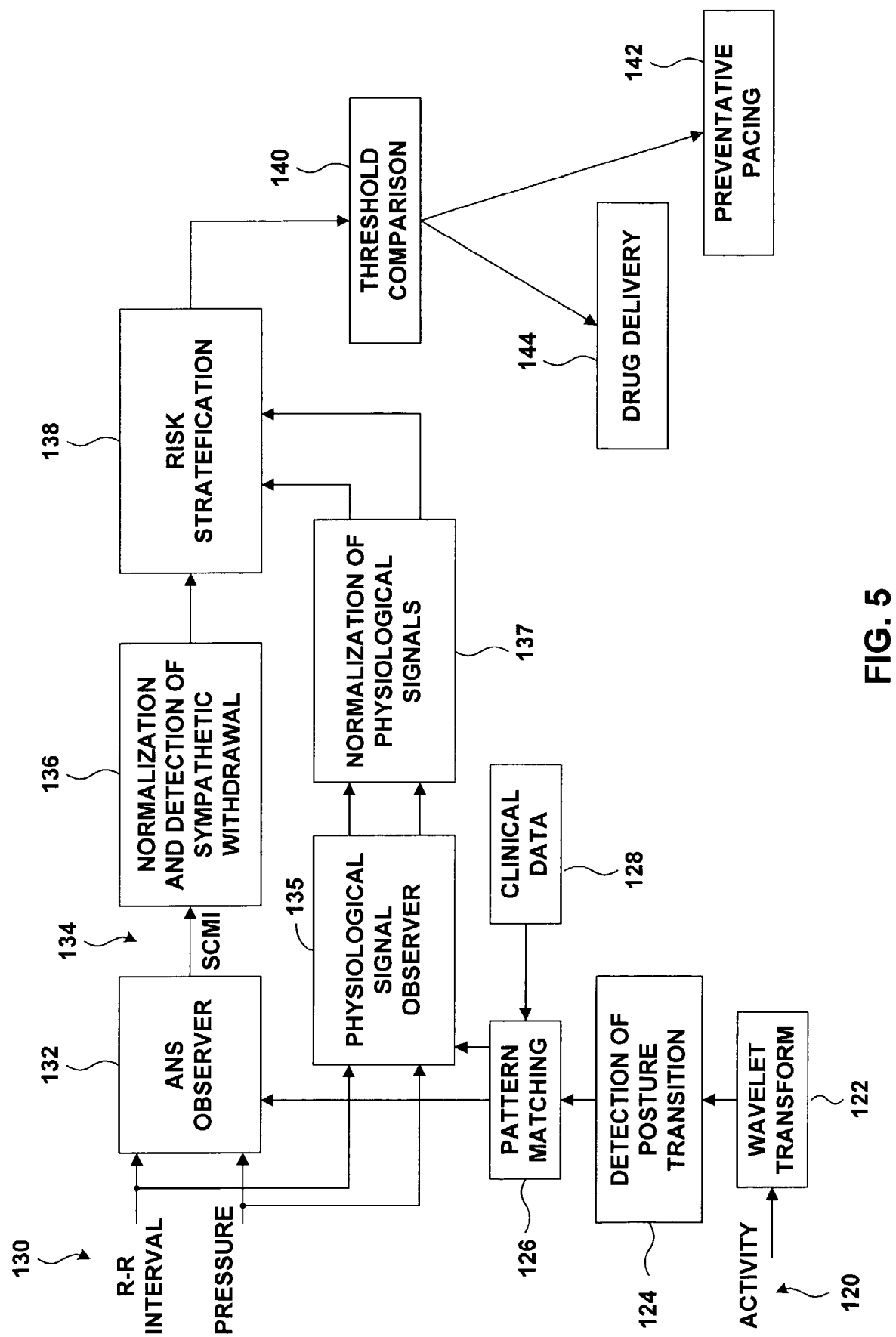
FIG. 5 is a block diagram illustrating the flow of information in an exemplary embodiment of a system that practices the invention

A technique illustrated in FIG. 5, however, has been demonstrated to be an effective technique for determining an indicator of ANS activity. FIG. 5 is a block diagram illustrating the flow of information in a system. In particular, FIG. 5 illustrates an exemplary technique for receiving inputs, determining an indicator of ANS activity, and assessing the risk of VVS. FIG. 5 also illustrates an exemplary technique for processing information related to the posture of the patient.

One input to the system is a signal or signals indicative of the activity 120 of the patient, as sensed by an activity sensor, such as activity sensor 50 in IMD 10. FIG. 5 depicts an exemplary process for analyzing signals indicative of patient activity 120. Signals indicative of patient activity 120 may be analyzed using wavelet analysis 122. Other analyses, such as Fourier analysis or morphological analysis, may be practiced as well. The purpose of analysis 122 to detect a posture transition 124, in particular, a posture transition that indicates increased orthostatic stress.

In the embodiment depicted in FIG. 5, a pattern-matching process 126 determines whether posture transitions detected by posture transition analysis 124 are the kinds of transitions that may lead to VVS. The patient's activity may be compared to clinical data 128 to determine the risk of VVS. For example, when analysis of the transition indicates a transition from a supine position to an upright position, such a transition increases orthostatic stress and may lead to VVS. When analysis of the transition indicates a transition from a supine position to a prone position, however, such a transition usually results in no significant increase in orthostatic stress and is unlikely to lead to VVS.

A posture transition that may lead to VVS triggers analysis of the ANS activity. As depicted in FIG. 5, analysis of ANS activity includes receiving at least two physiological signals 130 that include at least one indicator of ANS activity. As noted above, such signals include, but are not limited to, the R-R interval, the Q-T interval, and blood pressure. In FIG. 5, the R-R interval and blood pressure are shown as exemplary physiological signals 130. The analysis of ANS activity may further take into account a normalization of ANS activity, as described below in connection with FIGS. 5 and 6. The analysis may further take into account normalized physiological signals such as heart rate and blood pressure.

An ANS observer 132 receives physiological signals 130, and generates one or more signals 134 that indicate ANS activity. ANS observer 132 may be implemented by a processor such as microcomputer circuit 54 in IMD 10, and may be triggered by pattern-matching process 126. In FIG. 5, ANS observer 132 generates a signal 134 that indicates cardiac ANS activity, denoted as the sympathetic cardiac modulation index (SCMI). In general, the SCMI reflects the sympatho-vagal balance, with a high SCMI indicating cardiac sympathetic dominance, and a low SCMI indicating cardiac parasympathetic dominance. SCMI 134 is one example of an indicator of ANS activity, but the invention is not limited to this indicator. Nor is the invention limited to a single indicator. The invention encompasses embodiments, for example, in which ANS observer 132 generates distinct signals reflecting sympathetic nervous activity and parasympathetic nervous activity. The indicator or indicators of ANS activity may be determined by signal processing techniques. One technique for extracting one or more indicators from input physiological signals 130 is blind source separation (BSS).

BSS is a well-known technique for determining original signals from mixtures of signals. Physiological signals 130 are the sources that include mixtures of sympathetic and parasympathetic signals. By applying BSS, ANS observer 132 separates or "demixes" physiological signals 130 to reconstruct the sympathetic and parasympathetic signals or SCMI signal 134. Physiological signals 130 may be filtered prior to BSS.

The invention is not limited to determining indicators of sympathetic or parasympathetic activity applying BSS. Other signal processing techniques may be employed to determine one or more indicators of ANS activity. Determining one or more ANS indicators from BSS, however, is advantageous in that it is a robust technique for recovery of signals from noisy sources and it is suitable for recovery of temporally correlated signals such as SCMI signal 134. BSS therefore is well suited to detection of sympathetic withdrawal that may precede an episode of VVS.

During a monitoring period that begins with the detection of a posture transition that may lead to VVS, a measure of an ANS indicator is generated. SCMI signal 134 is normalized 136 with respect to the measure, i.e., with respect to the signals observed during the monitoring period. Normalization in this fashion helps make the SCMI subject-independent. This technique will be described below in connection with FIG. 6.

During the monitoring period, physiological signals 130 may be supplied to a physiological signal observer 135 for observation. Observer 135 may filter physiological signals 130 and may generate one or more measures of the signals, such as the mean and variance. Physiological signals 130 received after the monitoring period may be normalized 137 with respect to the measures. A processor such as microcomputer circuit 54 in IMD 10 may generate the a measure of an ANS indicator, may generate the a measure of the physiological signals, and may normalize the signals with respect to the respective measures.

A processor such as microcomputer circuit 54 in IMD 10 estimates the probability 138 that the patient will experience VVS. The estimation may be based upon the normalized indicator or indicators of ANS activity, the normalized physiological signals, and the posture transition experienced by the patient. The processor compares the risk of VVS to a threshold 140, and when the risk exceeds the threshold, the processor directs the delivery of therapy. The processor may control a therapy module, such as a preventative pacing system 142 or drug delivery system 144, to deliver therapy.

The threshold may be a programmable parameter. The invention is not limited to any particular threshold. The threshold may be, for example, a percentage of likelihood, or an indicator of positive or negative risk.

Figure 6:
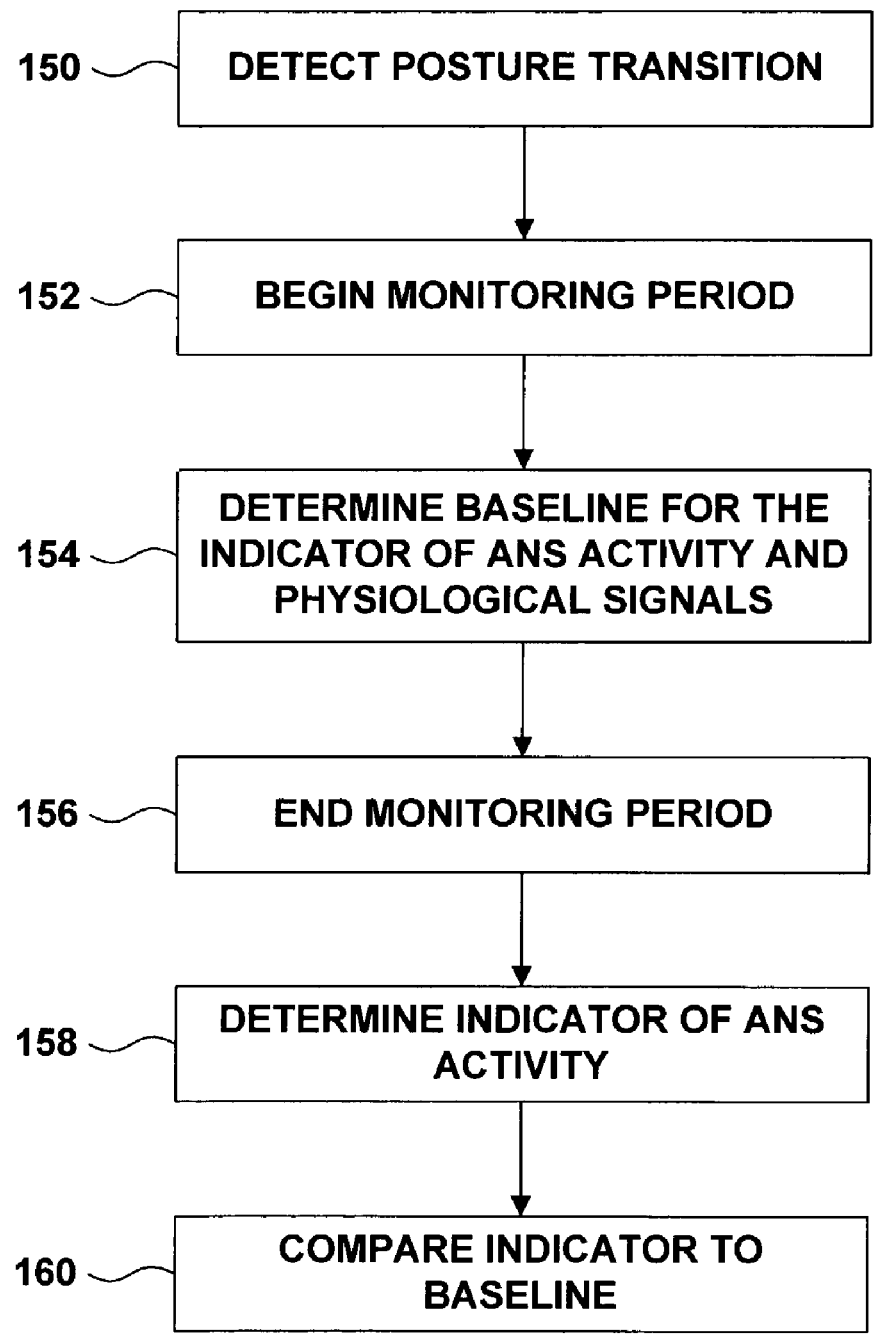
FIG. 6 is a flow diagram illustrating techniques for determining a baseline indicator of autonomic nervous system activity.

FIG. 6 is a flow diagram illustrating a technique for normalization 138 depicted in FIG. 5. In general, normalization may include determining a baseline of ANS activity during a monitoring period that follows detection of posture transition. It has been discovered that persons at risk of recurrent episodes of VVS do not experience fainting for several minutes after the change in posture, and that the ANS requires time to adjust following the posture change. Accordingly, a processor such as microcomputer circuit 54 may safely monitor ANS activity for during a monitoring period and may determine a baseline. Whether a withdrawal of sympathetic nervous activity has occurred may then be determined in reference to the baseline activity. In general, the baseline represents a cumulative measure of an indicator of ANS activity and physiological signals, rather than a single measurement taken at a single time during the monitoring period.

Normalization may also include normalizing physiological signals 130 with respect to baseline determined during the monitoring period. The baseline may comprise one or more measures of the physiological signals, such as the mean and variance.

Following a detected posture transition (150), the monitoring period begins (152). A typical monitoring period may be, for example, from 180 to 200 seconds, during which the risk of VVS onset is low. During the monitoring period, a processor determines a baseline indicator of physiological signals 130 and ANS activity (154). The baseline value of ANS activity may be determined by the techniques described above, i.e., receiving two physiological signals that indicate ANS activity, and applying BSS to demix the sympathetic and parasympathetic components or to recover a single signal that reflects ANS activity, such as SCMI 134. A processor may, for example, compute a mean value of an ANS index during the monitoring period, along with the variance, and the mean and variance may serve as the baseline. The baseline may be stored in a memory module, such as memory units 62 or 68 of IMD 10. A processor may further compute a mean and variance of the physiological signals.

When the monitoring period ends (156), the processor determines the indicator of ANS activity (158). Once again, the indicator of ANS activity may be determined by the techniques such as receiving two physiological signals that indicate ANS activity, and applying BSS to recover one or more indicators of ANS activity. The physiological signals may be normalized to the baseline determined during the monitoring period. The processor further compares the indicator of ANS activity to the baseline (160). By this comparison, the processor may estimate the probability that the patient will experience VVS. This probability may be further compared to a threshold as described above, and therapy may be administered as a function of the comparison to the threshold.

Figure 7:
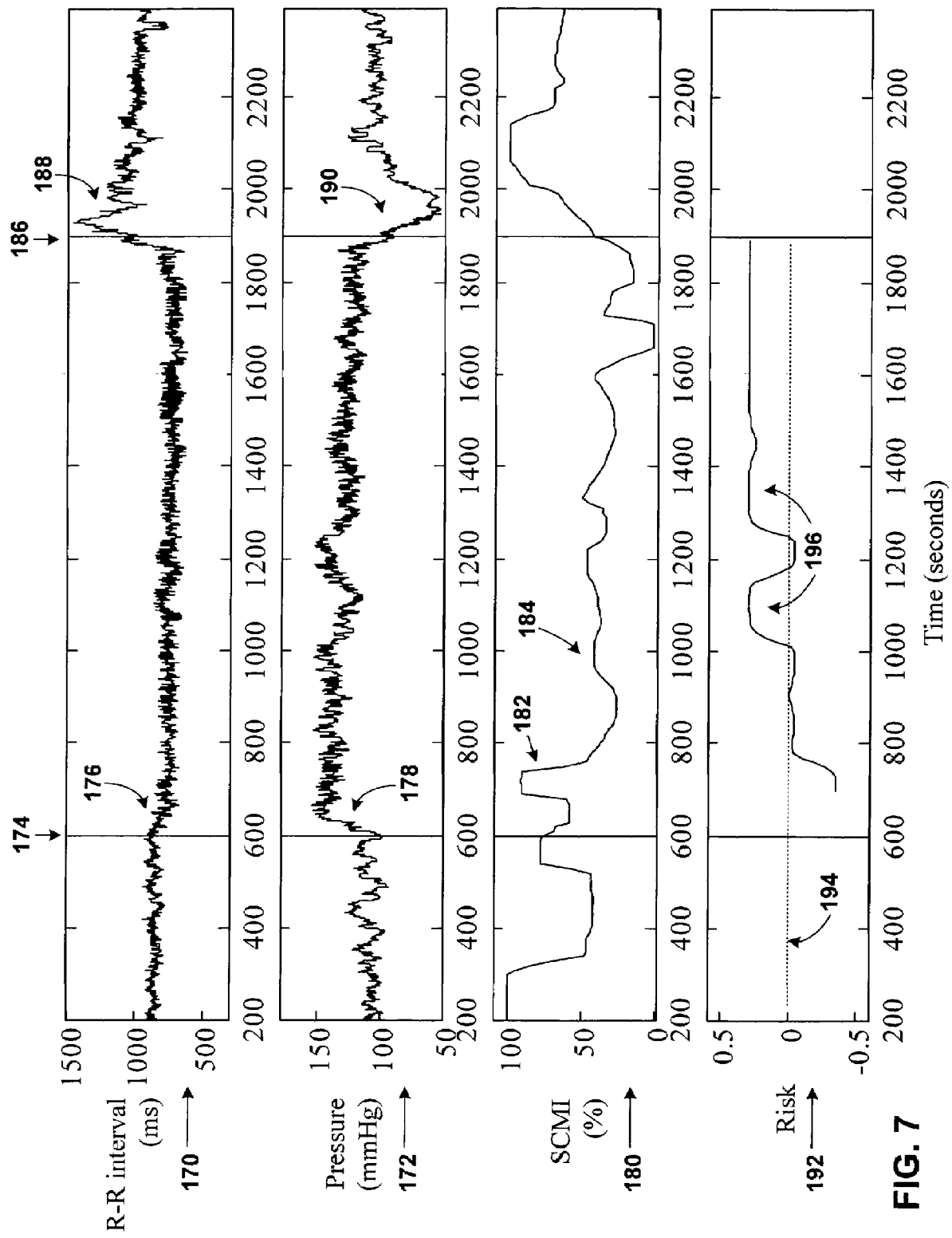
FIG. 7 shows four exemplary timelines illustrating the relationship among posture transition, physiological signals that include indicators of autonomic nervous system activity, and the onset of VVS, and further illustrating use of the techniques of the invention to make an early detection of the onset of VVS.

FIG. 7 includes four timelines on the same time scale. These timelines illustrate an exemplary operation of the invention. Timeline 170 represents the R-R interval, as measured by IMD 10 or another medical device. Timeline 172 represents a blood pressure such as arterial blood pressure. The time reference 174 at approximately t=600 seconds represents the detection of a posture transition. The posture transition triggers the beginning of the monitoring period, and further triggers analysis of the R-R interval and the pressure to determine a baseline indicator of ANS activity. In FIG. 7, the duration of the monitoring period is 200 seconds.

Following the posture transition, the R-R interval shows a decrease 176, meaning that the heart of the patient is beating more rapidly. The blood pressure presents an increase 178 following the posture transition. ANS activity, however, is not obvious from the R-R interval and the pressure. By applying BSS, a processor may separate the physiological signals to reconstruct the sympathetic and parasympathetic signals. In FIG. 7, ANS activity is represented by a single index, SCMI 180. In general, a high SCMI indicates cardiac sympathetic dominance, and a low SCMI indicates cardiac parasympathetic dominance.

Following the posture transition, the patient exhibits notable sympathetic activity 182 during the monitoring period. Near the end of the monitoring period or following the monitoring period, however, the sympathetic activity exhibits a decline 184. The patient does not experience VVS immediately as a result of this decline, but experiences VVS at time reference 186 at approximately t=1900 seconds, when the patient experiences a marked increase in R-R interval (i.e., a marked drop in heart rate) 188, and a marked drop in blood pressure 190.

By monitoring sympathetic withdrawal with respect to the baseline determined during the monitoring period, the processor assesses the risk 192 that the patient will experience VVS. Any scale of risk may be employed. In FIG. 7, risk is rated as positive or negative, with zero representing the threshold 194.

By applying therapy when the patient is at positive risk of VVS 196, the episode of VVS at time reference 186 may be avoided. Notably, positive risk of VVS manifests itself well before the actual onset of VVS. Therapy such as preventative pacing may therefore be more effective because they may be applied well before the onset of an episode of VVS.

The invention may offer one or more advantages, in addition to earlier application of therapy to prevent VVS. The techniques of the invention offer a robust and reliable predictor of VVS episodes, so patients are at risk of recurrent episodes of VVS are less likely to experience such episodes. The techniques of the invention are generally more robust and reliable than other techniques for predicting VVS, such as monitoring of heart rate variance.

In addition, because many patients at risk of recurrent VVS suffer from bradycardia or other heart conditions that may be treated with a pacemaker, the techniques of the invention may be practiced by a device that is already implanted in the body of the patient. The patient may be provided additional hardware, such as a pressure sensor, to carry out the techniques of the invention. Additional hardware is not required in all cases, however.

A number of embodiments of the invention have been described. However, one skilled in the art will appreciate that the invention can be practiced with embodiments other than those disclosed. For example, the invention may be practiced in devices other than the specific devices described herein. An implantable or external drug delivery apparatus, for instance, may include an activity sensor to detect a posture transition and a processor to determine an indicator of ANS activity and estimate the probability that the patient will experience VVS.

There are many techniques for determining an indicator of ANS activity. The techniques specifically described herein are robust and reliable, but other techniques may be practiced with the invention as well.

The invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software. These and other embodiments are within the scope of the following claims.

What is claimed is:

1. A method comprising:
   detecting a posture transition of a patient;
   monitoring autonomic nervous system activity of the patient for a defined period in response to detecting the posture transition;
   determining a baseline indicator of the autonomic nervous system activity during the monitoring period;
   following the monitoring period, continuing monitoring of the autonomic nervous system activity of the patient during a subsequent period;
   determining, based upon monitoring during the subsequent period, an indicator of an autonomic nervous system activity of the patient;
   comparing the indicator based upon monitoring during the subsequent period to the baseline indicator; and
   estimating a probability that the patient will experience vasovagal syncope as a function of the comparing step.

2. A method according to claim 1, wherein detecting a posture transition comprises detecting a posture transition that increases orthostatic stress.

3. A method according to claim 1, wherein determining the indicator of the autonomic nervous system activity comprises determining a sympatho-vagal balance.

4. A method according to claim 1, wherein determining the indicator of the autonomic nervous system activity comprises determining at least one of cardiac sympathetic nervous activity and cardiac parasympathetic nervous activity.

5. A method according to claim 1, wherein determining the indicator of the autonomic nervous system activity comprises:
   detecting at least one physiological signal that includes a sympathetic activity indicator and a parasympathetic activity indicator;
   determining the sympathetic activity indicator;
   determining the parasympathetic activity indicator; and
   estimating the relative magnitude of the sympathetic activity indicator in comparison to the parasympathetic activity indicator.

6. A method according to claim 5, further comprising:
   detecting at least a second physiological signal that includes the sympathetic activity indicator and the parasympathetic activity indicator; and
   applying blind source separation to the physiological signals to determine the sympathetic activity indicator and the parasympathetic activity indicator.

7. A method according to claim 5, wherein the physiological signal comprises at least one of a heart rate, a heart interval and a blood pressure.

8. A method according to claim 1, wherein the baseline indicator of the autonomic nervous system activity comprises a cumulative measure of the indicator of the autonomic nervous system activity and at least one physiological signal during the monitoring period.

9. A method according to claim 1, wherein determining the baseline indicator comprises sensing at least one physiological signal.

10. A method according to claim 9, wherein the physiological signal comprises at least one of a heart rate, a heart interval and a blood pressure.

11. A method according to claim 1, further comprising:
    sensing at least one physiological signal during the monitoring period;
    generating a measure of the physiological signal as a function of the sensing during the monitoring period;
    sensing the physiological signal following the monitoring period; and
    normalizing the physiological signal following the monitoring period with respect to the measure.

12. A method according to claim 1, further comprising normalizing the indicator to the baseline indicator.

13. A method according to claim 1, further comprising:
    sensing at least one physiological signal; and
    determining the indicator of an autonomic nervous system activity of the patient as a function of the physiological signal.

14. A method according to claim 1, further comprising the step of delivering a therapeutic output to the patient based on a comparison of the probability to a threshold.

15. A method according to claim 14, wherein the step of delivering step occurs if the probability exceeds the threshold.

16. A computer-readable medium comprising instructions for causing a programmable processor to:
    detect a posture transition of a patient;
    monitor autonomic nervous system activity of the patient for a defined period beginning upon detecting the posture transition;
    determine a baseline indicator of the autonomic nervous system activity during the monitoring period;
    following the monitoring period, continuing to monitor the autonomic nervous system activity of the patient during a subsequent period;
    determine, an indicator of autonomic nervous system activity of the patient based upon monitoring during the subsequent period;
    comparing the indicator to the baseline indicator; and
    estimate the probability that the patient will experience vasovagal syncope as a function of the comparing step.

17. A medium according to claim 16, wherein the instructions causing the processor to detect a posture transition of a patient comprise instructions causing the processor to detect a posture transition that increases orthostatic stress.

18. A medium according to claim 16, wherein the instructions causing the processor to determine the indicator of the autonomic nervous system activity comprise instructions causing the processor to determine a sympatho-vagal balance.

19. A medium according to claim 16, wherein the instructions causing the processor to determine the indicator of the autonomic nervous system activity comprise instructions causing the processor to determine at least one of cardiac sympathetic nervous activity and cardiac parasympathetic nervous activity.

20. A medium according to claim 16, wherein the instructions causing the processor to determine the indicator of the autonomic nervous system activity comprise instructions causing the processor to:
    detect at least one physiological signal that includes a sympathetic activity indicator and a parasympathetic activity indicator;
    determine the sympathetic activity indicator;
    determine the parasympathetic activity indicator; and
    estimate the relative magnitude of the sympathetic activity indicator in comparison to the parasympathetic activity indicator.

21. A medium according to claim 20, the instructions further causing the processor to:
    detect at least a second physiological signal that includes the sympathetic activity indicator and the parasympathetic activity indicator; and apply blind source separation to the physiological signals to determine the sympathetic activity indicator and the parasympathetic activity indicator.

22. A computer readable medium according to claim 16, further comprising instructions for causing a programmable processor to deliver a therapeutic output to the patient based on a comparison of the probability to a threshold.

23. A computer readable medium according to claim 22, wherein the programmable processor delivers the therapeutic output if the probability exceeds the threshold.

24. A device comprising:
a first sensor adapted to detect a posture transition of a patient and provide a posture transition signal upon detecting the posture transition;
a second sensor to sense a physiological signal that includes an indicator of autonomic nervous system activity; and
a processor, configured to:
monitor the physiological signal during a defined period following detection of the posture transition;
determine a baseline indicator of the autonomic nervous system activity during the monitoring period; following the monitoring period, continue monitoring the autonomic nervous system activity of the patient during a subsequent period and
determine based upon monitoring during the subsequent period the indicator of autonomic nervous system activity;
wherein the device further comprises further comprising a memory module adapted to store the baseline indicator of the autonomic nervous system activity; characterized in that the processor is further configured to compare the indicator based upon monitoring during the subsequent period to the baseline indicator and to estimate the probability that the patient will experience vasovagal syncope as a function of the comparison.

25. A device according to claim 24, wherein the first sensor comprises an accelerometer.

26. A device according to claim 24, wherein the processor is further configured to determine a sympathetic activity indicator from a physiological signal, determine a parasympathetic activity indicator from the physiological signal and estimate the relative magnitude of the sympathetic activity indicator in comparison to the parasympathetic activity indicator.

27. A device according to claim 26, further comprising a third sensor to sense a second physiological signal that includes an indicator of autonomic nervous system activity, wherein the processor is further configured to apply blind source separation to the first and second physiological signal to determine the sympathetic activity indicator and the parasympathetic activity indicator.

28. A device according to claim 24, wherein the second sensor comprises at least one of a heart rate sensor, a heart interval sensor and a blood pressure sensor.

29. A device according to claim 24, wherein the processor is further configured to deliver a therapeutic output to the patient based on a comparison of the probability to a threshold.

30. A device according to claim 29, wherein the processor delivers the therapeutic output if the probability exceeds the threshold.

* * * * *

UNITED STATES PATENT AND TRADEMARK OFFICE
CERTIFICATE OF CORRECTION

PATENT NO. : 7,647,106 B2
APPLICATION NO. : 10/422069
DATED : January 12, 2010
INVENTOR(S) : Nathalie Virag et al.

It is certified that error appears in the above-identified patent and that said Letters Patent is hereby corrected as shown below:

Column 13
Line 29, delete "further comprises".

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,647,106 B2
APPLICATION NO. : 10/422069
DATED : January 12, 2010
INVENTOR(S) : Virag et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 748 days.

Signed and Sealed this

Sixteenth Day of November, 2010

David J. Kappos
*Director of the United States Patent and Trademark Office*